United States Patent [19]

Johnson et al.

[11] Patent Number: 4,618,769
[45] Date of Patent: Oct. 21, 1986

[54] LIQUID CHROMATOGRAPHY/FOURIER TRANSFORM IR SPECTROMETRY INTERFACE FLOW CELL

[75] Inventors: Charles C. Johnson, Fairfield, Ohio; Larry T. Taylor, Blacksburg, Va.

[73] Assignee: The United States of America as represented by the United States Department of Energy, Washington, D.C.

[21] Appl. No.: 689,104

[22] Filed: Jan. 4, 1985

[51] Int. Cl.$^4$ ............................ G01J 1/00; G01N 1/10
[52] U.S. Cl. ..................................... 250/338; 250/341; 356/246; 356/440
[58] Field of Search .................... 250/338 R, 339, 341; 356/440, 246

[56] References Cited

U.S. PATENT DOCUMENTS

| | | | |
|---|---|---|---|
| 3,985,441 | 10/1976 | Schoeffel et al. | 356/246 |
| 4,009,964 | 3/1977 | Bergen | 356/246 |
| 4,229,179 | 10/1980 | Lee | 356/246 |
| 4,405,235 | 9/1983 | Rossiter | 356/440 |

OTHER PUBLICATIONS

Hirschfeld, "Dynamic Range Improvement in Fourier Transform Infrared Spectrometry", *Anal. Chem.* 50, 1978.
Brown et al., "Microbore Liquid Chromatography with Flow Cell Fourier Transform Infrared Spectrometric Detection", *Anal. Chem.* 55, 1983.
Johnson et al., "Zero Dead Volume Flow Cell for Microbore Liquid Chromatography with Fourier Transform Infrared Spec. Detection, *Anal. Chem.* 56, Dec. 1984.
Johnson et al., Tenth Quarterly Progress Report for Period, Jan. 1984—Mar. 1984, published Jun. 1984.

*Primary Examiner*—Janice A. Howell
*Attorney, Agent, or Firm*—Hugh W. Glenn; Robert J. Fisher; Judson R. Hightower

[57] ABSTRACT

A zero dead volume (ZDV) microbore high performance liquid chromatography ($\mu$HPLC)/Fourier transform infrared (FTIR) interface flow cell includes an IR transparent crystal having a small diameter bore therein through which a sample liquid is passed. The interface flow cell further includes a metal holder in combination with a pair of inner, compressible seals for directly coupling the thus configured spectrometric flow cell to the outlet of a $\mu$HPLC column end fitting to minimize the transfer volume of the effluents exiting the $\mu$HPLC column which exhibit excellent flow characteristics due to the essentially unencumbered, open-flow design. The IR beam passes transverse to the sample flow through the circular bore within the IR transparent crystal, which is preferably comprised of potassium bromide (KBr) or calcium fluoride ($CaF_2$), so as to minimize interference patterns and vignetting encountered in conventional parallel-plate IR cells. The long IR beam pathlength and lensing effect of the circular cross-section of the sample volume in combination with the refractive index differences between the solvent and the transparent crystal serve to focus the IR beam in enhancing sample detection sensitivity by an order of magnitude.

12 Claims, 11 Drawing Figures

LIQUID CHROMATOGRAPHY/FOURIER TRANSFORM IR SPECTROMETRY INTERFACE FLOW CELL

CONTRACTUAL ORIGIN OF THE INVENTION

The U.S. Government has rights in this invention under Contract No. DE-FG22-81PC40799 between the Department of Energy and Virginia Polytechnic Institute and State University, Blacksburg, Va.

BACKGROUND OF THE INVENTION

This invention relates generally to infrared spectrometer detectors in general and is particularly directed to a liquid sample flow cell for directly interfacing with a microbore high performance liquid chromatography/Fourier transform infrared spectrometer.

The use of a Fourier transform infrared (FTIR) spectrometer as a detector for high performance liquid chromatography (HPLC) is well known in the art. Recently, microbore HPLC columns have been used in combination with FTIR spectrometers. Microbore HPLC spectrometers offer three primary advantages over conventional FTIR detectors. First, the substantial decrease in required sample, e.g., approximately 20-fold, less in microbore columns below analytical scale columns substantially enhances the detectability of species. This is particularly important when working with limited sample sizes. In addition, the low solvent consumption of microbore columns allows for the economical testing of various potential IR solvents which would otherwise be cost prohibitive. Finally, the microbore HPLC approach offers high detection limits and the possibility for individual compound separation and identification by FTIR of very complex mixtures without the previous associated large solvent consumption.

Referring to FIG. 1, there is shown an exploded view of a prior art sealed, parallel plate interface flow cell 10 for use in microbore HPLC/FTIR systems. The parallel plate interface flow cell 10 is comprised of a first window 12, a second window 22 and a metal spacer 14 interspaced therebetween. The first and second windows 12, 22 are typically comprised of potassium bromide (KBr) and the thickness of the metal spacer 14 establishes the IR pathlength through the interface flow cell. In this arrangement, the sample as well as the effluent are introduced into a first aperture 24 in the second window 22 and flow through the "keyhole" arrangement of a first flow channel 18, a center aperture 16 and a second flow channel 20 within the metal spacer 14 and exit through a second aperture 26 within the second window 22. An IR beam is directed through the first and second windows 12, 22 and through the center aperture 16 of the metal spacer 14 for providing a spectral analysis of the sample flowing therethrough. The primary disadvantage of this interface flow cell arrangement is the circuitous sample/effluent flow path of the sealed cell and its complexity in terms of the various gaskets and tubing necessary for connection. The unswept or mixing volume is exhibited in chromatographic measurements as a chromatographic peak characterized by a tailing response. In addition, the off-axis location of the first and second apertures 24, 26 within the second window 22 relative to the first and second flow channels 18, 20 in the metal spacer 14 produces a region of dead volume in which eddy currents are generated resulting in the aforementioned chromatographic peak exhibiting a tailing response.

In spite of these limitations, the prior art seal interface flow cell 10 shown in FIG. 1 was believed to be the optimum design for interfacing with a liquid chromatography/Fourier transform IR spectrometer because it provided a single path length for the IR beam and thus obeyed Beer's law with respect to the absorption of light traversing a given cell length. It was thought that a non-planar interface cell configuration would not obey Beer's law and thus would not afford consistent and predictable IR beam absorption characteristics.

The present invention is intended to avoid the aforementioned limitations of the prior art by providing a liquid chromatography/Fourier transform IR spectrometry interface flow cell which essentially eliminates stagnate or eddy currents in the sample/effluent flow path for more accurate measurements. In addition, the circular cross-section of the liquid sample serves as a focusing lens due to the refractive index differences between the solvent and the interface flow cell crystal structure in minimizing interference patterns and vignetting observed in conventional parallel-plate infrared cells.

OBJECTS AND SUMMARY OF THE INVENTION

Accordingly, the present invention is intended to provide improved sample detection in an infrared spectrometer.

Another object of the present invention is to provide a spectrometric flow cell for directly interfacing with a high performance liquid chromatography/Fourier transform infrared spectrometer having a zero dead volume sample flow characteristic and improved IR beam focusing.

Yet another object of the present invention is to provide a zero dead volume microbore high performance liquid chromatography/Fourier transform IR spectrometry interface flow cell which affords low sample and effluent volume, long IR beam pathlength, unencumbered flow geometry to minimize dead volume, and minimal connection tubing between the column outlet and the illuminated region.

A further object of the present invention is to substantially reduce effluent volume in a microbore high performance liquid chromatography/Fourier transform infrared spectrometer and thus decrease sample and solvent waste therein.

These and other objects are accomplished by the present invention which contemplates a zero dead volume (ZDV) microbore high performance liquid chromatograph/Fourier transform infrared spectrometry ($\mu$HPLC/FTIR) interface flow cell comprised of an IR transparent crystal, such as of potassium bromide (KBr) or calcium fluoride ($CaF_2$) in a preferred embodiment, with a small diameter circular bore therein through which the sample flows. The crystal is provided with an inert, compressible seal, such as of TEFLON, on respective ends thereof so as to form a spectrometric flow cell which is directly coupled to the outlet of a microbore HPLC column. This flow cell provides the interface necessary not only to satisfy the IR spectrometric requirement of a reasonable pathlength, but also to address the microbore chromatographic constraint of minimal dead zone by providing an essentially unencumbered, open-flow design. Coupling the HPLC column directly to the interface flow cell of the present invention limits the transfer volume of the effluents into the IR-illuminated region to that volume within the end fitting of the column and within the gasket seal which may be paper-thin so as to to contribute an insignificant volume compared to the volume arising from an end fitting which also provides required mechanical strength. The geometry of the interface flow cell results in the entire transfer volume being swept cleanly according to laminar flow and is characterized by a zero dead volume.

A narrow circular bore within the transparent crystal through which the sample flows presents a circular cross-section to the 90° incident IR beam and thus, due to the refractive index differences between the solvent and the IR transparent crystal, serves as a focusing lens for the use of commercially available beam condensing optics. In addition, the circular cross-section of the sample minimizes interference patterns and vignetting encountered in conventional prior art parallel plate IR cells.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, in which:

DETAILED DESCRIPTION OF THE PREFERRED EMBODIMENT

Figure 2:
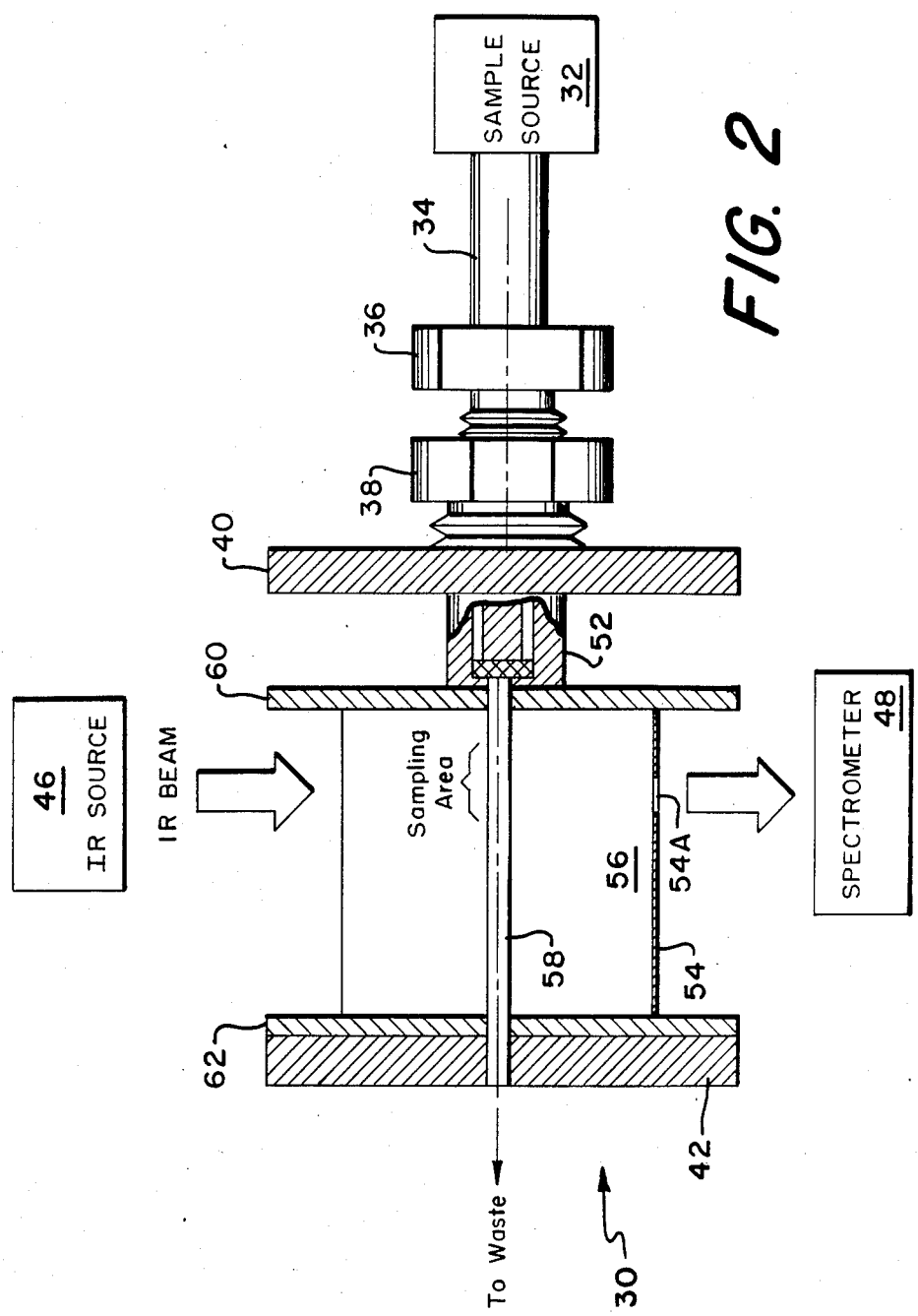
FIG. 2 is a simplified schematic diagram of a liquid chromatography/Fourier transform IR spectrometry interface flow cell in accordance with the prsent invention.

Referring to FIG. 2, there is shown in simplified schematic form a liquid chromatography/Fourier transform IR spectrometry interface flow cell 30 in accordance with the present invention. The interface flow cell 30 is coupled to a sample source 32 by means of a microbore HPLC column 34. An IBM LC/9533 ternary gradient liquid chromatograph is included in the sample source 32 for delivering solvent to the interface flow cell 30. A Rheodyne Model 7413 injector equipped with a 0.5 microliter loop is connected to the interface flow cell 30 for chromatographic studies via a 0.007 inch inner diameter×4 cm length of stainless steel tubing to a 1 mm inner diameter×50 cm microbore HPLC column 34 packed with 10 micrometers of Silica Gel. The column efficiency was measured at 12,500 plates.

The interface flow cell 30 includes an IR transparent crystal 56 comprised of a block of either $CaF_2$ or KBr and approximately 10×10×6 mm in size with a 0.75 mm cylindrical bore 58 drilled through it. The IR transparent crystal 56 is sealed in place using an EM Science microbore end fitting 38 which threadably engages a first lateral portion 40 of a metal holder. A second lateral portion 42 of the metal holder is positioned on an opposite side of the IR transparent crystal 56 to permit the microbore column end fitting 38 to compress a pair of TEFLON gaskets 60, 62 on opposite, facing surfaces of the IR transparent crystal 56 when tightened. "TEFLON" is a trademark of Du Pont Company of Wilmington, Del., as applied to hard plastics comprised of polytetrafluoroethylene resins. The microbore column end fitting 38 is threadably engaged by means of a microbore HPLC column coupler 36 by means of which it is securely coupled to the microbore HPLC column 34. Located on an inner portion of the first lateral portion 40 of the metal holder is a bore coupler 52 for coupling the bore 58 within the IR transparent crystal 56 with the microbore HPLC column 34 so as to form a continuous channel through which a mixture of the sample under analysis and an elution solvent is directed for the purpose of spectrographic analysis of the sample.

An IR source 46 is positioned generally perpendicular relative to the direction of sample and elution solvent movement so as to direct an IR beam at essentially a 90° angle relative to the flow path. The IR beam transits the IR transparent crystal 56 and is incident upon the sample under investigation in the area generally labeled Sampling Area within the IR transparent crystal 56, with the IR beam which exits the IR transparent crystal 56 containing information regarding the IR characteristics of the sample under investigation. The IR beam thus transmitted through the IR transparent crystal 56 is provided to a spectrometer 48 for spectrometric analysis of the composition of the sample under investigation. The shape of the spectrometric viewing region, or Sampling Area, is circular in cross-section and exerts a "lensing" effect in focusing the IR beam. This feature of the present invention minimizes interference patterns and vignetting, or the gradual shading off of the image into the surrounding background, generally experienced in the prior art. This focusing effect arises not only from the cross-sectional shape of the Sampling Area, but also because of the refractive index differences between the solvent which transits the Sampling Area and the IR transparent crystal 56. The IR beam is generally on the order of the diameter of the bore 58 within the IR transparent crystal 56, e.g., on the order of 0.75 mm in diameter, permitting the use of commercially available beam condensing optics and providing for increased throughput properties because of the aforementioned lensing effect.

A Nicolet 6000C FTIR spectrometer equipped with a narrow-band Model 7010A mercury-cadmium-telluride detector (MCT-A) is used to monitor the effluents in the flow cell. The standard Nicolet software package is used to collect time resolved, 4 cm$^{-1}$ resolution spectra. The time resolution between each collected interferogram is 0.65 seconds. For the 5-component mixture separation shown in FIG. 5 and discussed below, every four scans are co-added and stored in a file for post-run data manipulation. Interferograms are averaged post-run using the co-addition routine which weights the files that are averaged so that computationally each interferogram carries equal weight. Since the focal diameter of the Nicolet 6000C is 3 mm and the bore within the IR transparent crystal 56 is 0.75 mm in diameter, a Barnes Model 600 4X beam condenser (not shown) is used to reduce the focal diameter to approximately 0.75 mm. The aluminum metal holder comprised of coupled first and second lateral portions 40, 42 includes provisions for adjusting the alignment of the interface flow cell 30 with the incident IR beam. Alignment of the cell is facilitated by filling the interface flow cell 30 with a solvent and adjusting its location until the observed interferogram exhibits a minimum signal (peak-to-peak) at the center burst. An opaque mask 54 having an aperture 54A therein through which the IR beam passes may be positioned on the surface of the crystal 56 adjacent to the spectrometer 48 for decreasing IR beam loss from the crystal. However, the opaque mask 54 is not essential for proper operation of the present invention.

The following analysis was used to optimize the signal-to-noise ratio of the IR spectrum generated by the interface flow cell 30 of the present invention. If it is assumed that a chromatographic peak is Gaussian in shape, then the concentration profile of the sample, or analyte, with time in the chromatographic peak can be described by the normal curve, as follows:

$$\phi(x) = \frac{1}{2\pi} e^{-x^2/2} \qquad (1)$$

where $x = t/\sigma_t$, $t$ = amount of time from the peak maximum (where $t=0$), and $\sigma_t$ = standard deviation of the peak. The FTIR spectrometer 48 can scan with time resolution typically much faster than the chromatographic response time. By saving individual interferograms, a time-resolved histogram of spectra can be obtained as the peak elutes. By starting at the chromatographic peak maximum and co-adding the spectra symmetrically on either side of the maximum, the co-added file will contain a composite spectrum of the average concentration ($C_{obs}$) of analyte over the time interval of co-addition. Expressed mathematically, $$C_{obs} = \frac{A_x}{2x} = \frac{1}{2x} \int_{-t}^{+t} \phi(x)dx = \frac{1}{x} \int_{0}^{t} \phi(x)dx \qquad (2)$$

where $A_x$ = area under the normal curve. The values for this integral are available from well-known mathematical tables.

Incoherent noise contributions to the spectrum can be diminished by co-addition of repetitive scans with the noise decreasing mathematically as the inverse of the square root of the number of scans co-added. Since the signal observed by the IR spectrometer 48 is proportional to the observed concentration in the interface flow cell 30, then the signal-to-noise ratio can be described as follows:

$$S/N \propto n^{\frac{1}{2}} C_{obs}, \text{ where } n = \text{the number of scans coadded} \qquad (3)$$

Figure 3:
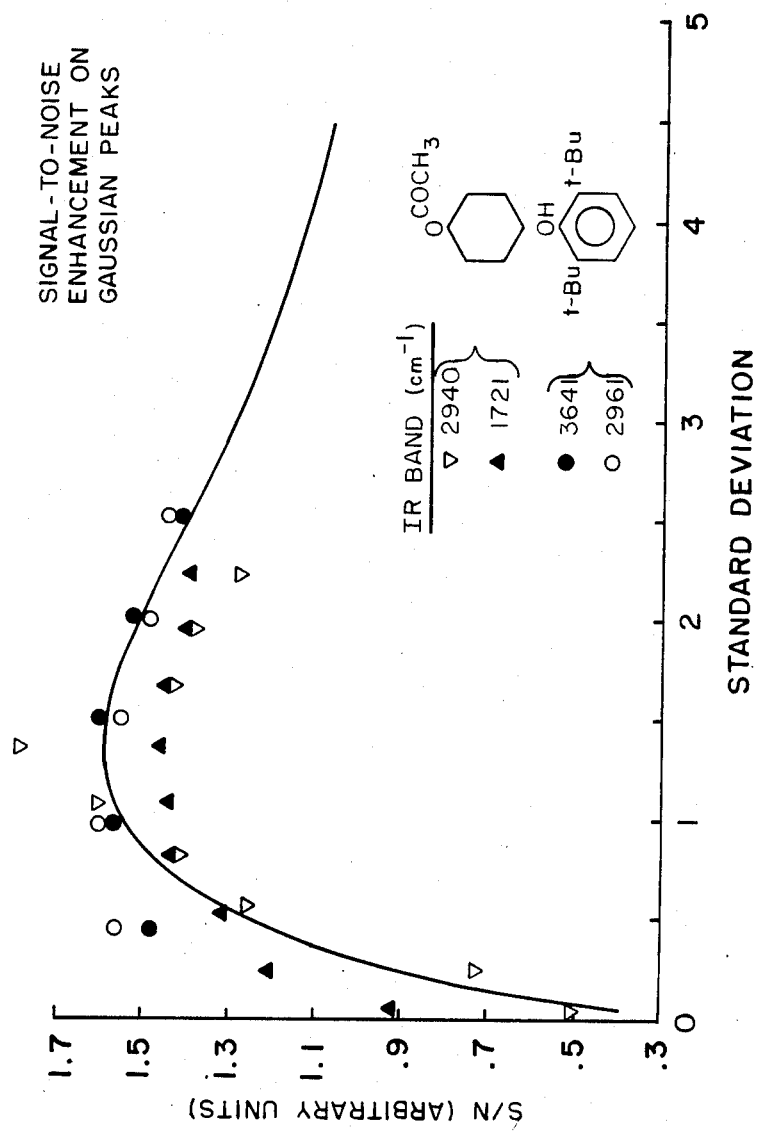
FIG. 3 is a graphic illustration of the signal-to-noise ratio as a function of the amount of a Gaussian peak used for co-addition in the form of a solid theoretical curve and a plurality of measured signal-to-noise points normalized to an arbitrary scale for cyclohexyl acetate and 2,6-di-tert-butylphenol for a spectrometric interface flow cell in accordance with the present invention.

While it would be expected that the signal-to-noise ratio would increase as long as the co-addition of scans enhanced the observed concentration and/or diminished the observed noise of the composite spectrum, at some point the co-addition of scans should approach a limiting noise value such that further co-addition of the low concentration spectral scans at the edges of the chromatographic peak simply dilutes the observed analyte concentration. At this point, the signal-to-noise ratio is diminished. This trend is graphically illustrated in FIG. 3 which makes use of the previous equations and represents a theoretical signal-to-noise ratio plotted as a function of the amount ($\pm X\sigma$), of a Gaussian peak used for co-addition where the solid line represents the theoretical curve, and the plotted points represent the measured signal-to-noise ratio (normalized to an arbitrary scale) for cyclohexyl acetate and 2,6-di-tert-butylphenol. It can be shown that the relative time per scan is irrelevant to the curve maximum at $X = \pm 1.37\sigma$. For practical reasons, the peak should be defined in time resolution where $4\sigma$ equals a minimum of 10 scans. This would indicate that the maximum signal-to-noise spectrum would be obtained by co-adding seven of these scans which are symmetrical about the peak maximum.

Figure 4:
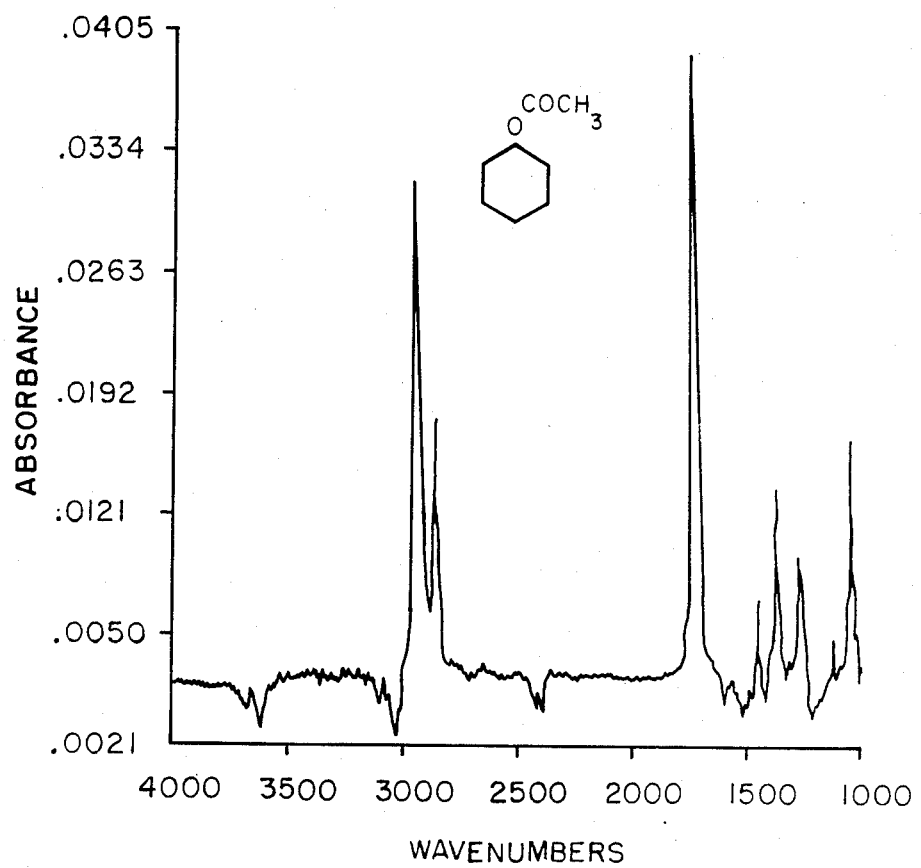
FIG. 4 illustrates the IR spectrum of five micrograms of cyclohexyl acetate injected into a 0.009 inch inner diameter×65 cm length tubing using chloroform as the elution and with FTIR detection at 47 micro L/minute in an interface flow cell containing a calcium fluoride crystal in accordance with the present invention.

Experimental data supporting the theoretical approach described above are shown in FIGS. 3 and 4. FIG. 4 shows the measured spectrum using a liquid chromatography/Fourier transform IR spectrometry interface flow cell 30 in accordance with the present invention of cyclohexyl acetate in chloroform wherein 5 micrograms was injected into a 0.009 inch inner diameter × 65 cm length tubing, zero dead volume CaF$_2$ flow cell with FTIR detection at 47 microliters/minute and with scans co-added $\pm 1.4\sigma$ about peak maximum. The measured values shown in FIG. 4 are plotted in FIG. 3 and show good agreement between theoretical and experimental signal-to-noise ratios of the interface flow cell arrangement of the present invention. In addition, experimental data relating to the elution with chloroform at 45 microliters/minute of 2,6-di-tert-butylphenol from a microbore silica column was monitored with an interface flow cell in accordance with the present invention with the results also plotted in FIG. 3. These experimental results also show close agreement with the theoretical signal-to-noise curve shown therein.

Figure 1:
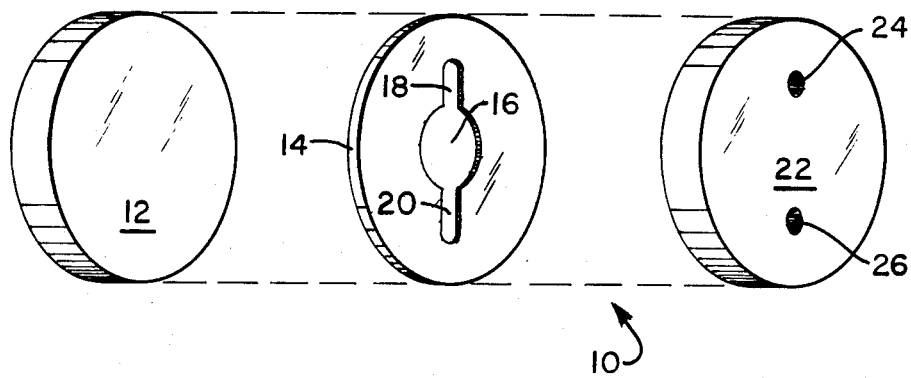
FIG. 1 is a simplified exploded, schematic diagram of a conventional prior art parallel plate IR spectrometry interface flow cell.

The interface flow cell 30 for the present invention is characterized as providing an enhanced pathlength/volume ratio and a decreased cell volume over that previously available in conventional parallel plate interface flow cells as shown in FIG. 1. The pathlength of the IR beam through the interface flow cell 30 of the present invention is not only more than doubled over that available in the prior art, but the cell volume is decreased by an order of magnitude. The increased pathlength afforded by the present invention substantially increases spectrometric measurement sensitivities, while the decreased cell volume allows the use of microbore liquid chromatography, consequently reducing the amount of required eluting components which are generally expensive and thus increase the cost of spectrometer measurements. A liquid chromatography/Fourier transform IR spectrometer system utilizing an interface flow cell in accordance with the present invention can easily provide a pathlength/volume ratio of 1.36.

The IR transparent crystal 56 can be made from a variety of infrared-transparent materials such as $CaF_2$ or KBr. The smoother the inner surface of the bore 58, the less the incident IR beam will be scattered. It has been suggested that ultrasonic drilling may provide a much smoother internal surface, although the mechanically-drilled bore 58 within the interface flow cell 30 provides a high level of measurement accuracy.

Figure 5:
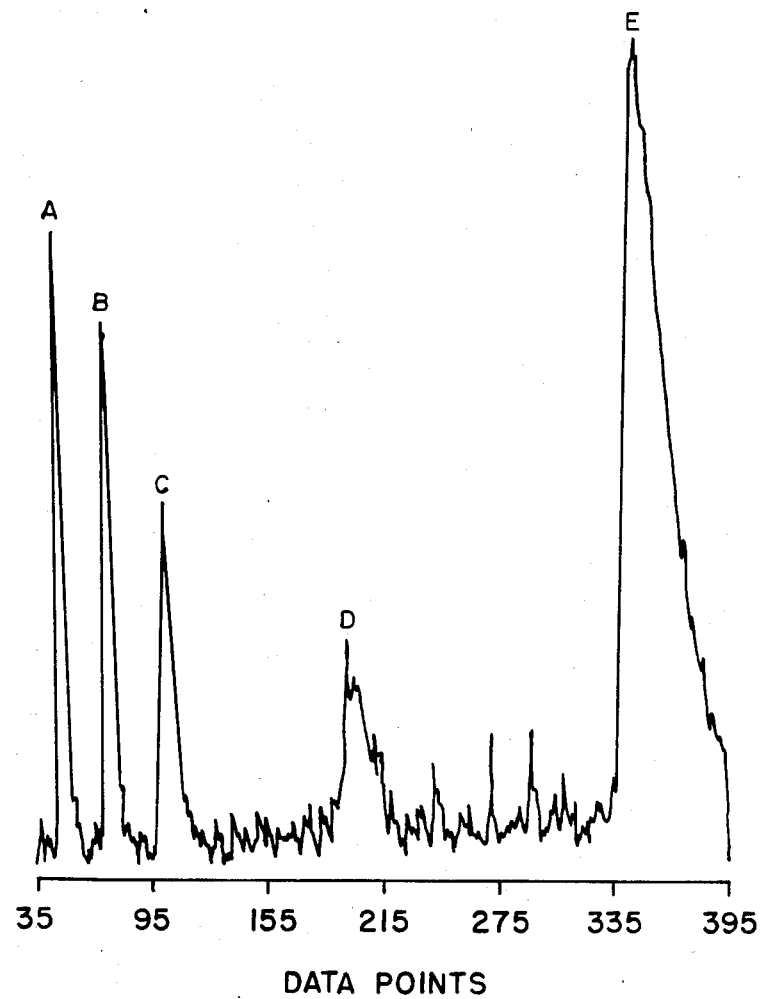
FIG. 5 is a Gram-Schmidt based reconstructed chromatogram taken with an interface flow cell in accordance with the present invention for a five-component separation of (A) 2,6-di-tert-butylphenol, (B) o-methoxybiphenyl, (C) 2-tert-butylphenol, (D) 2-sec-butylphenol, and (E) cyclohexyl acetate (in the order of elution) on silica gel with chloroform elution.
Figures 6A, 6B:
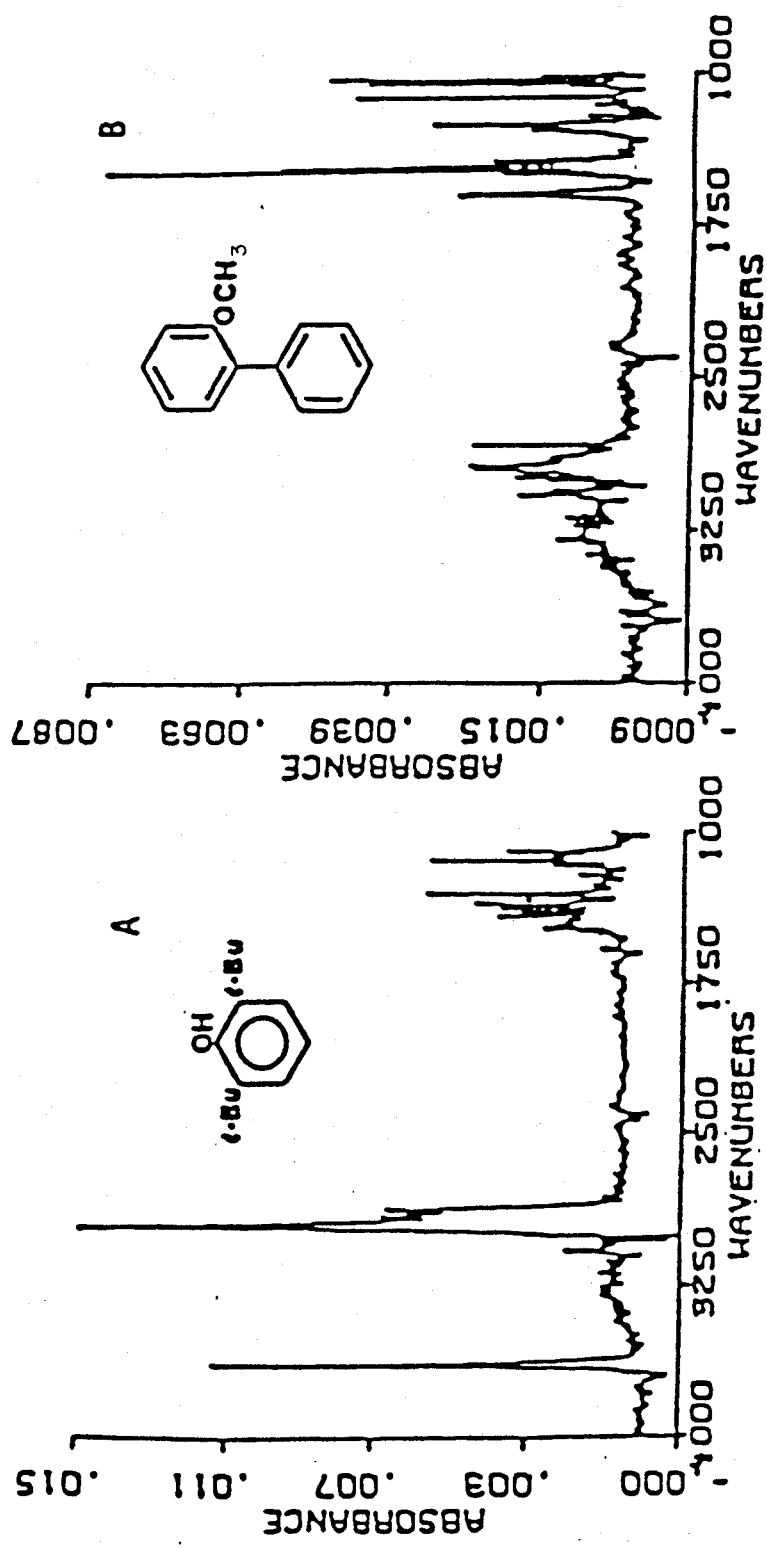
FIGS. 6A–6E illustrate the spectra of the various components separated in the chromatogram of FIG. 5 using a spectrometric flow cell in accordance with the present inventon.
Figures 6C, 6D:
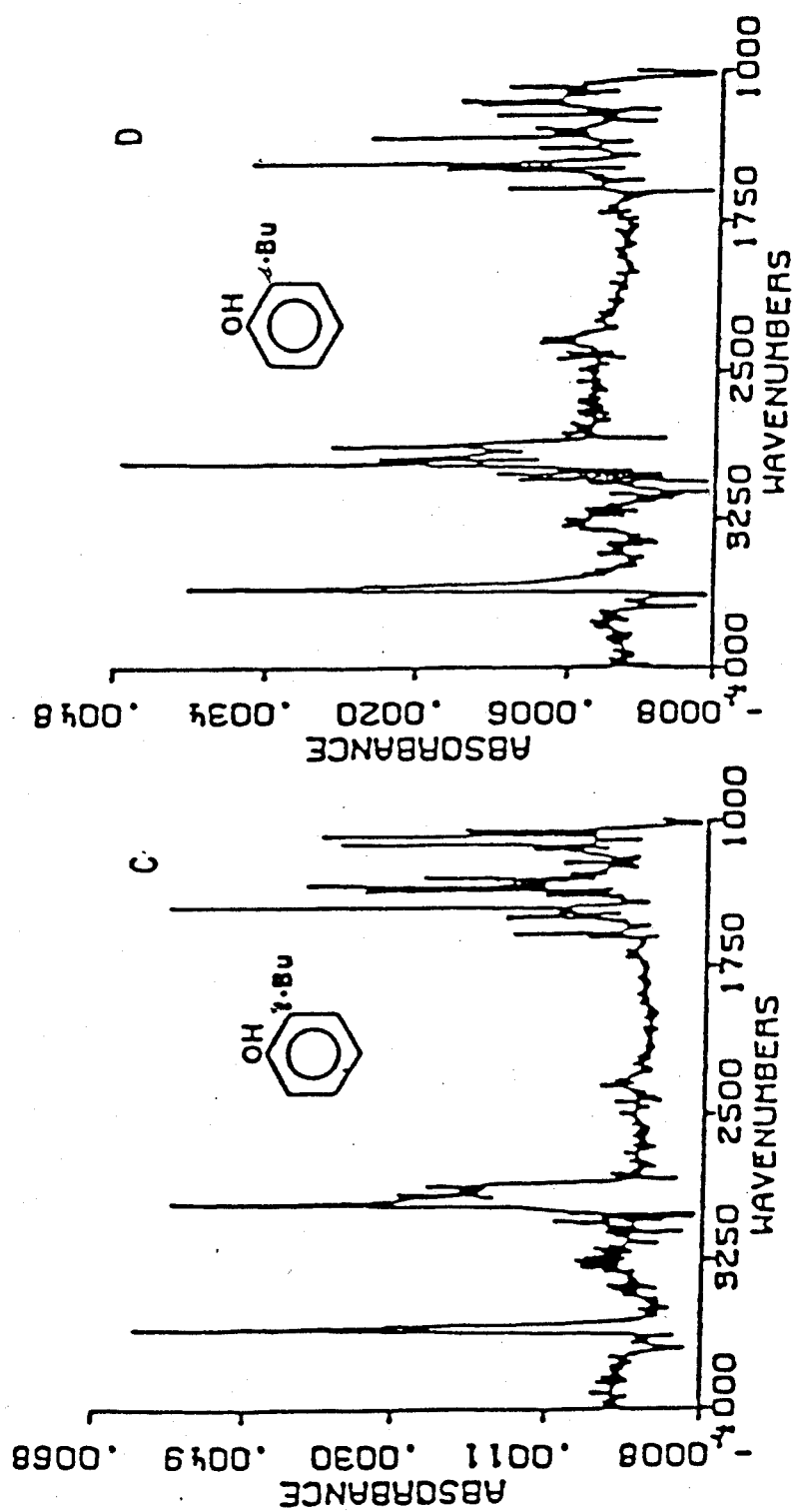
Figure 6E:
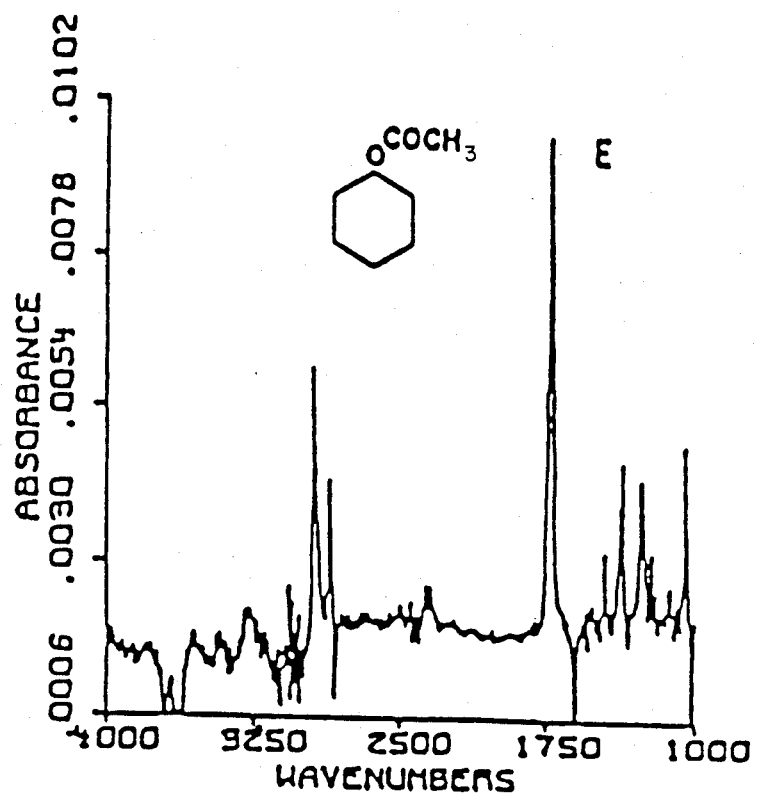

Referring to FIG. 5, there is shown the results of a 5-component separation using an interface flow cell 30 in a liquid chromatography/Fourier transform IR spectrometer arrangement in accordance with the present invention. The five components separated are: (A) 2,6-di-tert butylphenol, (B) o-methoxybiphenyl, (C) 2-tert-butylphenol, (D) 2-sec-butylphenol, and (E) cyclohexyl acetate (in the order of elution) on silica gel with chloroform elution. The Gram-Schmidt reconstructed chromatograph of FIG. 5 shows a reasonable signal for all five components, particularly for cyclohexyl acetate. Despite the dilution of this compound at a k' of nearly 3.0, the interferogram has such a distinct change from the base line interferograms that a very large response is observed. This is probably due to the large absorptivity of the carbonyl stretch. The 5-component chromatogram shown in FIG. 5 represents an injection of five micrograms of each component within a 0.5 microliter injection loop, which is well within the capacity of a 1 mm inner diameter $\times$ 50 cm microbore column.

The file spectra obtained from the 5-component separation illustrated in FIG. 5 are shown in FIGS. 6A-6E using a co-addition of files $\pm 1.37\sigma$ around each peak maximum. All of the spectra shown in FIGS. 6A-6E are characterized as providing good signal-to-noise ratios and each contains sufficient information to readily identify the compound by comparison to library spectra taken in the same solvent. Using the interface flow cell 30 of the present invention in a liquid chromatography/Fourier transform IR spectrometry arrangement eliminates the broad, multiple bands expected at major solvent absorbances and the requirement of a background blanking routine. Small perturbations in the baseline occur at those regions where chloroform bands exist, namely 3660–3710 cm$^{-1}$, 3000–3080 cm$^{-1}$, 2380–2440 cm$^{-1}$, 1580–1625 cm$^{-1}$, 1240–1250 cm$^{-1}$, 1170–1180 cm$^{-1}$, and 1020–1000 cm$^{-1}$. These chloroform bands, considering the pathlength of the interface flow cell 30, are consistent with previously generated "optimal pathlength" diagrams.

Operationally in the present invention, a background spectrum of solvent within the interface flow cell 30 is collected as an interferogram in the distance domain and stored. At the appropriate time, a spectrum is collected and stored of both the sample and the solvent within the interface flow cell 30. After the chromatographic run is completed, the interferograms are retrieved from the disc and individually Fourier processed by a computer (not shown) in a conventional manner. This includes phase calculation, apodization, Fourier transformation and final phase correction. The result is a single-beam transmission spectrum of each file. Strong solvent bands in the infrared give rise to virtually no throughput, while weaker bands merely attenuate the throughput at each characteristic frequency. Ideally, if the sample spectrum had only solvent in it, the single-beam spectra of the sample and the background would be identical. A normal percent transmission spectrum can be obtained by dividing each data point in the sample spectrum by the corresponding point in the background spectrum. One would expect the resulting spectrum to be featureless and uniformly exhibit 100% transmission, or T.

Mathematically, however, regions in which the solvent is opaque to infrared radiation result in response values in the single-beam spectra of zero. Thus, when the % transmission spectrum is obtained, those IR regions near solvent bands are calculated as a ratio of two numbers very close to zero. Obviously if the numerator is non-zero, division by zero is unattainable. Division of a small number, say $10^{-3}$ units, by a much smaller number, say $10^{-9}$, gives $10^6$ as a result. If the numerator and denominator are interchanged, $10^{-6}$ is obtained. Slight noise fluctuations causing minor differences such as these around solvent bands can give rise to very large deviations from the 100% transmission line, both positively and negatively. Consequently, if one plots an infrared spectrum of a strongly IR absorbing solvent, broad, multiple bands, which are essentially amplified noise, are observed in regions of solvent opacity.

The interface flow cell 30 of the present invention, on the other hand, is cross-sectionally circular. Solvent absorbances in the infrared are not affixed to a single pathlength. On the contrary, the solvent slice at the center of the flow cell 30 gives rise to absorbances characteristic of 0.75 mm pathlength, whereas, the slices at the edge of the flow cell give rise to absorbances characteristic of pathlengths approaching zero. Since the infrared beam is not forced using masks or slits to traverse the cell at only the long pathlength regions, the detector "sees" the average signal across the entire cell. Sufficient throughput is therefore observed at the edges of the interface flow cell 30 to add an offset to the single-beam spectra.

Using the previous mathematical example, if the offset at a particular solvent band is $10^{-1}$ units in a single beam spectrum, and we use the values of $10^{-3}$ for sample and $10^{-9}$ for background, the ratio of the offset plus sample to offset plus background results in a value of 101% transmission. If, because of noise variations, the two are switched, a value of 99% transmission is obtained. Thus, the interface flow cell of the present invention avoids the problems associated with solvent absorbance while prior art parallel plate cells merely amplify noise contributions in regions of high solvent absorbance. It should be noted that even though these artifacts are not observed, these regions nevertheless remain opaque to dissolved, IR absorbing analytes.

By adding an offset to the single-beam spectra, however, it is evident that Beer's law linearity may be suspect. On the other hand, it has been shown that by simultaneously measuring infrared spectra at multiple pathlengths, the dynamic range, particularly at low and high signal-to-noise regions of the spectrum, is enhanced. If the geometry of the interface cell 30 were to increase the dynamic range, especially by enhancing the detectability at low concentrations in the liquid chromatography/Fourier transform IR spectrometer, the inconvenience of constructing detailed calibration curves to correct for nonlinearity would be well worth the effort.

Figure 7:
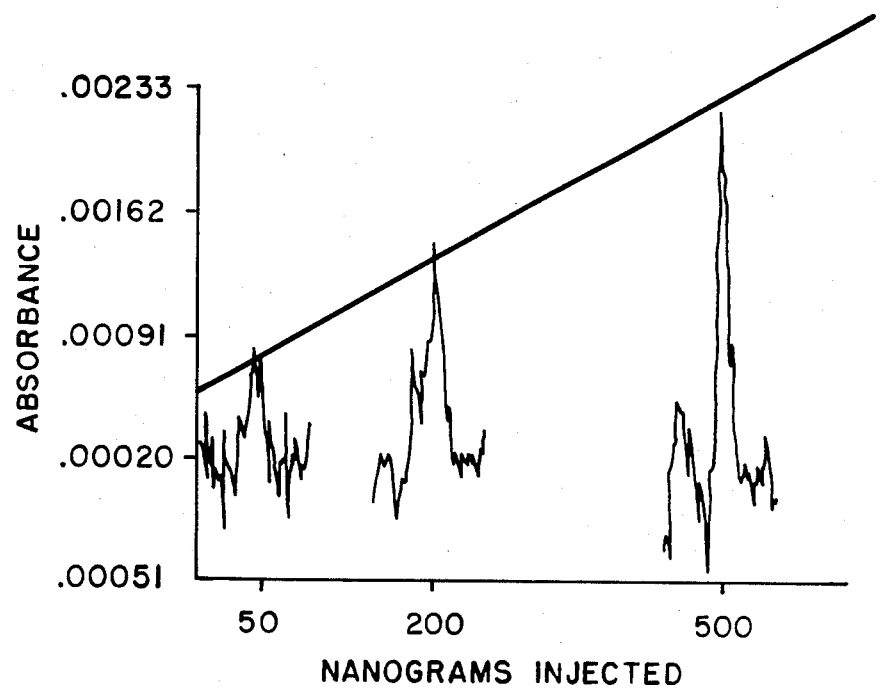
FIG. 7 illustrates the minimum detectable quantity of 2,6-di-tert-butylphenol measured in a liquid chromatography/Fourier transform IR spectrometry interface flow cell in accordance with the present invention.

A study to determine the detection limits of 2,6-di-tert-butylphenol was undertaken using both the interface flow cell 30 of the present invention and the optimal peak area co-addition technique previously described. A summary of the results for the hydroxyl stretch (3641 cm$^{-1}$) is given in Table I. Numerical analysis of the data not only demonstrates excellent linearity (r=0.997), but also gives a detection limit of 37 ng, which is a significant improvement over the previously available detection (1670 ng) limit for 2,6-di-tert-butylphenol employing this vibrational mode. FIG. 7 shows a plot of the lowest three amounts injected as well as the spectra at the hydroxyl stretch region where these measurements were taken. It is apparent that the detection limit is indeed below 50 ng. Significantly lower detection limits are expected using the asymmetric methyl bend at 1426 cm$^{-1}$ where the FTIR detector sensitivity is greater.

TABLE I

| Amount Injected (ng) | A (3641 cm$^{-1}$) | $N_{RMS}$ (3500-3575 cm$^{-1}$) |
|---|---|---|
| 50 | 0.000538 | 0.000161 |
| 200 | 0.001541 | 0.000122 |
| 500 | 0.002156 | 0.000178 |
| 1000 | 0.004049 | 0.000170 |
| 2500 | 0.01229 | 0.000170 |
| 5000 | 0.02156 | 0.000231 |

There has thus been shown a liquid chromatography/Fourier transform IR spectrometry interface flow cell which provides low cell volume, a long IR beam path length, unencumbered effluent flow geometry to minimize dead volume, and minimal connection tubing between a microbore high performance liquid chromatography column outlet and the sampling area. These characteristics permit the interface flow cell of the present invention to provide more accurate and sensitive spectrometric measurements than previously available.

While particular embodiments of the present invention have been shown and described, it will be obvious to those skilled in the art that changes and modifications may be made without departing from the invention in its broader aspects. For example, the IR transparent crystal may have virtually any cross-sectional shape. However, a circular cross-section for the crystal would increase the aforementioned "lensing" effect upon the IR beam and thus provide an even further increase in detection sensitivity. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. In a Fourier transform infrared spectrometer wherein a sample material is isolated by liquid chromatography and directed through an elongated tube of small inner diameter for irradiation by an infrared beam in obtaining an infrared spectrum of the sample material representing the composition thereof, a sample flow cell comprising:
   a generally cylindrical crystal having a longitudinal axis and a generally circular cross-section, wherein said crystal is transparent to infrared radiation and is positioned in line with the infrared beam with its longitudinal axis aligned generally perpendicular to the infrared beam, whereby said infrared beam is incident upon said crystal and is focused generally on the crystal's longitudinal axis and is transmitted therethrough so as to exit therefrom; and
   a small diameter, linear bore having a circular cross-section positioned within said crystal along the longitudinal axis and extending the length thereof and oriented generally perpendicular to the direction of propagation of the infrared beam therein, said bore coupled to the elongated tube for receiving and directing the sample material in the path of the infrared beam wherein the exiting infrared beam includes the infrared spectrum of the sample material.

2. An infrared spectrometer sample flow cell as in claim 1 further comprising gasket means positioned between a lateral surface of said crystal through which said bore extends and the elongated tube for coupling the elongated tube and said bore in a leak-proof manner.

3. An infrared spectrometer sample flow cell as in claim 2 wherein said gasket means is comprised of a hard plastic.

4. An infrared spectrometer sample flow cell as in claim 1 further including an IR beam source and a spectrometer positioned on respective sides of said crystal for respectively generating and receiving the IR beam.

5. An infrared spectrometer sample flow cell as in claim 4 further including means positioned on the side of said crystal adjacent to said spectrometer for directing the IR beam thereto.

6. An infrared spectrometer sample flow cell as in claim 5 wherein said means for directing the IR beam to said spectrometer includes an opqaue sheet having an aperture positioned adjacent to said spectrometer and through which the IR beam passes to said spectrometer.

7. An infrared spectrometer sample flow cell as in claim 1 wherein said crystal is comprised of KBr.

8. An infrared spectrometer sample flow cell as in claim 1 wherein said crystal is comprised of CaF$_2$.

9. An infrared spectrometer sample flow cell as in claim 1 further including cell holder means for coupling said crystal to the elongated tube, said cell holder means including coupling means for connecting said bore to the elongated tube in a linear arrangement.

10. An infrared spectrometer sample flow cell as in claim 9 further including first and second gasket means positioned between respective facing surfaces of said crystal and said cell holder means for forming a seal therebetween.

11. An infrared spectrometer sample flow cell as in claim 10 wherein said cell holder means includes first and second apertures in respective facing surfaces thereof through which the sample material enters and exits said crystal and which define respective ends of said bore.

12. An infrared spectrometer sample flow cell as in claim 1 wherein the IR beam and said bore have substantially equal width dimensions.

* * * * *